United States Patent [19]

Masson

[11] Patent Number: 4,762,795

[45] Date of Patent: Aug. 9, 1988

[54] DEVICE BASED ON AN INORGANIC CRYSTALLINE MATTER CONNECTED TO A SOURCE OF ENERGY AND USE OF SAID DEVICE FOR IMPROVING BACTERIAL METABOLISM

[76] Inventor: Alain Masson, La Besserie, 86130 Saint-Cyr, France

[21] Appl. No.: 868,620

[22] Filed: May 29, 1986

[30] Foreign Application Priority Data

May 30, 1985 [FR] France .................. 85 08147

[51] Int. Cl.⁴ .................. C12M 1/00; C12N 13/00
[52] U.S. Cl. .................. 435/287; 435/173; 435/3; 435/284; 435/288
[58] Field of Search .................. 435/284–286, 435/287, 289, 290, 801, 817, 3, 173

[56] References Cited

U.S. PATENT DOCUMENTS

| | | | |
|---|---|---|---|
| 3,618,734 | 11/1974 | Khan | 435/287 X |
| 3,660,242 | 5/1972 | Gordon et al. | 435/287 |
| 3,839,175 | 10/1974 | Keyes | 435/288 X |
| 4,347,222 | 8/1982 | Beall et al. | 435/287 X |
| 4,562,051 | 12/1985 | Stoermer, III et al. | 435/287 X |

FOREIGN PATENT DOCUMENTS

| | | |
|---|---|---|
| 815261 | 4/1937 | France . |
| 843994 | 4/1939 | France . |
| 2059215 | 3/1971 | France . |
| 2222433 | 10/1974 | France . |
| 1324403 | 7/1973 | United Kingdom . |

Primary Examiner—Larry Jones
Attorney, Agent, or Firm—Ladas & Parry

[57] ABSTRACT

This invention relates to a device constituted by a mixture of phyllosilicate and glucose powder, in which is embedded a filament connected to a source of alternating current. The mixture is contained in an inert envelope, the whole being contained in a container made of any material also containing the mixture and in which a test tube containing the culture medium is introduced.

19 Claims, 1 Drawing Sheet

DEVICE BASED ON AN INORGANIC CRYSTALLINE MATTER CONNECTED TO A SOURCE OF ENERGY AND USE OF SAID DEVICE FOR IMPROVING BACTERIAL METABOLISM

The present invention relates to a device used particularly for improving bacterial metabolism.

According to the invention, the device is constituted by a homogeneous mixture of an inorganic crystalline matter in powder form formed by octahedral and/or tetrahedral layers and of an amorphous (non-crystalline), organic material, said mixture being enclosed in an inert envelope and the whole being connected to a source of energy.

Among the crystalline matters which are suitable for the present invention, it has been found that the phyllosilicates alone or in mixture were particularly advantageous. Phyllosilicates present a lamellar structure and are constituted by sheets formed by tetrahedra and octahedra. Among these matters, mention may be made of kaolinite, serpentine, talc, mica, quartz. However, it is obvious that this list is not limiting.

Other matters, such as asbestos, may also be suitable.

In general, the absolute dielectrics are also suitable. The finely divided inorganic powder is mixed, preferably homogeneously, with an amorphous or non-crystalline material. Among these materials, carbohydrates such as glucose or its analogues will advantageously be chosen.

The whole is partially or totally enveloped in an inert envelope, preferably composed of cardboard, a sheet of plastics material or wood.

Among the sources of energy, electrical energy will advantageously be employed, sinusoidal (alternating current) or direct. Another appropriate form of energy may also be used.

An advantageous embodiment resides in a device characterized in that the source of electrical energy is constituted by a filament embedded in the mixture and connected to a source of alternating or direct current.

The intensity is preferably included between 0.1 mA and 10 A, the voltage between 0.1 and 100 V and, in the case of alternating current, the frequency is between 0.1 Hz and $2.10^9$ Hz. An intensity of between 0.1 and 1 A, a voltage between 1 and 10 V and a frequency of between 0.1 and 10 Mhz are preferably chosen. It has been found that the device described hereinabove made it possible substantially to increase the life duration of the bacteria of a culture medium when it was placed in the vicinity of this medium in an incubator making it possible to conserve the atmosphere appropriate for the development of the organisms.

The use of the device according to the invention is not limited to a particular family of bacteria and it may suit all bacteria.

The culture medium allowing bacteria to develop is well known to all microbiologists. It will simply be recalled that such organisms develop in a buffered aqueous medium whose pH is close to 7, at a temperature close to 37° C., in the pressure in particular of a source of carbohydrate.

With the device according to the invention, a considerable increase in the living bacterial population is observed in a very short time (less than 72 hrs.).

The device is, of course, not limited to this application, but is claimed as such.

The invention will be more readily understood on reading the following description of a particular embodiment which is to be considered solely by way of illustration and in no way limiting the invention, with reference to the accompanying drawings, in which.

Figure 1:
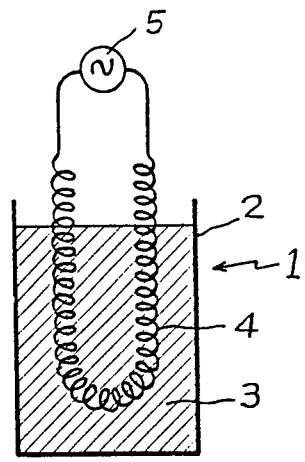
FIG. 1 is a view in longitudinal section of the device.
Figure 2:
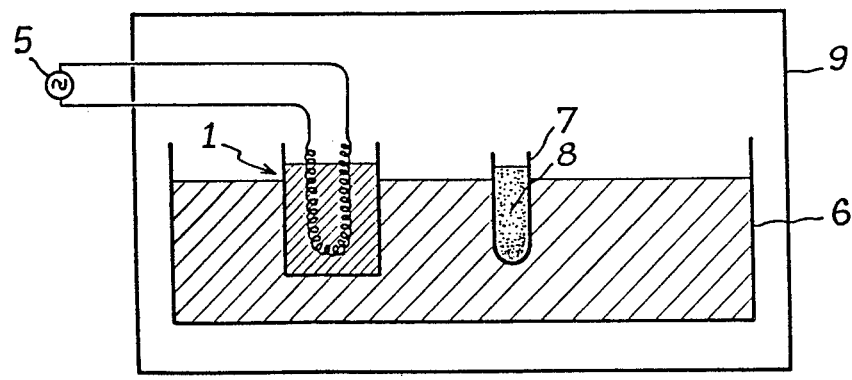
FIG. 2 is a view in longitudinal section of the device in the course of use.

Referring now to the drawings, FIG. 1 shows the device 1 constituted by an upwardly open cylindrical envelope 2 made of cardboard, containing up to a certain height the following mixture 3 of powder:

14.6% by weight of kaolinite
72.2% by weight of talc
13.2% by weight of glucose.

A spiral filament 4 is embedded in the powder and is connected to a source of alternating current 5. The envelope 2 is itself introduced in a container 6 made of any material which contains mixture 3 and in which is introduced a test tube 7 containing the culture medium 8. The container 6 is itself placed in an incubator 9.

The conditions of use are as follows:
intensity: 500 mA
alternating voltage: 5 V
frequency: 1 MHz The device according to the invention also offers the possibility of conditioning aqueous or organic liquids by placing the liquid in the vicinity of the device.

The invention will now be illustrated by examples employing different sorts of bacteria.

EXAMPLE 1

The bacterial strain is *Haemophilus influenzae* CNCM S2/52 serotype b., (filed by INSTITUT PASTEUR).

It is maintained by successive reseedings, in an appropriate liquid or solid medium and conserved in glycerined liquid medium, frozen to −80° C.

The culture medium is an Eugon nutrient solution buffered to pH 7.6 before sterilization, supplemented with growth factors. The V factor is supplied by a 0.2% (w/v) solution of β Nicotinamide adenine dinucleotide (Sigma) sterilized by filtration over membrane, added at the rate of 1% (v/v). The X factor is supplied by a 2% (w/v) solution of haemoglobin (Prolabo), precipitated and sterilized in an autoclave (15 mins. at 120° C.) added at the rate of 5% (v/v).

The liquid medium is sterilized in an autoclave for 15 mins. at 120° C. The numeration medium is a chocolate agar (Bio. Mérieux) to which Polyvitex enriching liquid is added.

The temperature of the tubes is 37±0.5° C. Seeding of the preculture nutrient solution is effected at the rate of 5% in tubes of 18×180 containing 20 ml of culture medium. This seeded volume is then divided into two equal fractions so that the contents of the two tubes participating in the test are at maximum identical.

Incubation is effected very rapidly in the incubator whose temperature has been stabilized for at least 24 hrs.

After 24, 48, possibly 72 hrs., 7 days and 14 days, 1 ml of each tube is taken for numerations.

Numeration is effected on the surface. The number is taken to the ml.

The test was repeated 15 times with numeration at times t=0, t=24 hrs., t=48 hrs. The results are shown in Tables I and II. Table I corresponds to the average values obtained as a function of the time whatever the value of the inoculum; Table II takes into account the value of the inoculum, the different values thereof being distributed in classes.

Each time, measurements are made with one of the test tubes not subjected to the action of the device.

TABLE I

Haemophilus influenza: number of living germs after 24 and 48 hrs. of incubation (average of 15 tests and confidence interval of 5%)

| Incubation time | Culture | |
|---|---|---|
| | Normal | Modified by the device |
| 24 hrs. | $1.3 + 0.6 \cdot 10^8$ | $1.9 + 0.2 \cdot 10^8$ |
| 48 hrs. | $3.4 + 1.3 \cdot 10^6$ | $31.4 \times 10.5 \cdot 10^6$ |

TABLE II

Haemophilus influenzae: number of living germs after 24 and 48 hrs. of incubation in normal atmosphere and modified depending on the importance of the inoculum

| | incubation time | | | |
|---|---|---|---|---|
| | 24 hrs. | | 48 hrs. | |
| | Culture | | | |
| Germs at $t = 0 \times 10^6$ | normal $\times 10^8$ | modified $\times 10^8$ | normal $\times 10^6$ | modified $\times 10^6$ |
| 0.87 | 1.2 | 1.63 | 3.60 | 15.00 |
| 1.15 | 1.25 | 1.54 | 3.70 | 14.50 |
| 1.42 | 1.16 | 1.58 | 4.00 | 16.00 |
| 1.50 | 1.40 | 2.80 | 0.69 | 23.00 |
| 1.65 | 1.20 | 1.65 | 3.10 | 13.00 |
| 2.44 | 0.50 | 1.84 | 1.18 | 18.00 |
| 3.23 | 0.63 | 2.14 | 1.13 | 21.00 |
| 4 | 0.76 | 1.60 | 0.82 | 17.00 |
| 4.43 | 0.79 | 1.90 | 8.60 | 63.00 |
| 4.9 | 1.60 | 2.40 | 6.50 | 52.00 |
| 6.2 | 4.90 | 2.50 | 0.60 | 13.00 |
| 6.6 | 0.32 | 1.40 | 3.40 | 52.00 |
| 8.6 | 1.55 | 1.80 | 4.50 | 55.00 |
| 12.6 | 0.52 | 1.60 | 2.70 | 46.00 |
| 14 | 1.70 | 2.10 | 6.50 | 52.00 |

EXAMPLE 2

The bacterial strain is *Listeria monocytogenes* CNCM 6089 serotype 4.

The treatment of this strain is identical to that of Example 1, apart from the fact that the Eugon nutrient solution is buffered to pH 7.2 before sterilization and the numeration medium is a casein soja agar (Merck) to which glucose is added at the rate of 5% (w/v).

Numeration is, in addition, effected in depth. The results are indicated in Table III hereinafter.

TABLE III

Listeria monocytogenes: number of living germs after 24, 48 and 72 hrs. of incubation in normal atmosphere and modified (average of three tests on 3 tubes and confidence interval of 5%)

| | Incubation time | | | | | |
|---|---|---|---|---|---|---|
| | 24 hrs. | | 48 hrs. | | 72 hrs. | |
| Test | Culture | | | | | |
| n° | normal | modified | normal | modified | normal | modified |
| I | $1.25 \cdot 10^9$ | $1.30 \cdot 10^9$ | $1.2 \cdot 10^8$ | $4.8 \cdot 10^8$ | $0.40 \cdot 10^6$ | $88 \cdot 10^6$ |
| II | $0.40 \cdot 10^9$ | $1.20 \cdot 10^9$ | $0.2 \cdot 10^8$ | $2.0 \cdot 10^8$ | $0.87 \cdot 10^6$ | $35 \cdot 10^6$ |
| III | $0.70 \cdot 10^9$ | $1.25 \cdot 10^9$ | $1.9 \cdot 10^8$ | $4.2 \cdot 10^8$ | $1.12 \cdot 10^6$ | $10.3 \cdot 10^6$ |
| average | $0.79 \cdot 10^9$ | $1.25 \cdot 10^9$ | $1.09 \cdot 10^8$ | $3.7 \cdot 10^8$ | $0.80 \cdot 10^6$ | $15 \cdot 10^6$ |
| interval of confidence (5%) | $0.40 \cdot 10^9$ | $0.06 \cdot 10^9$ | $0.70 \cdot 10^8$ | $1.3 \cdot 10^8$ | $0.33 \cdot 10^6$ | $32 \cdot 10^6$ |

EXAMPLE 3

The bacterial strain is *Escherichia coli* CNCM 54127.

The treatment of the strain is identical to that of Example 1, except for the fact that the nutrient solution is Trypticase Soja (Bio. Mérieux) for the precultures and a Proteose-peptone No. 3 nutrient solution (Difco) for the cultures and that the numeration medium is a casein soja agar (Merck) to which glucose is added at the rate of 5% (w/v).

Numeration is effected in depth. The results are shown in Table IV hereinafter.

TABLE IV

Escherichia Coli: number of living germs after 24, 72 hrs., 7 and 14 days of incubation in normal atmosphere and modified (average of 3 tests on 2 tubes and confidence interval of 5%)

| | Incubation time | | | | | | | |
|---|---|---|---|---|---|---|---|---|
| | 24 hrs. culture | | 72 hrs. culture | | 7 days culture | | 14 days culture | |
| Test No. | normal | modified | normal | modified | normal | modified | normal | modified |
| I | $1.6 \cdot 10^9$ | $2.2 \cdot 10^9$ | $0.8 \cdot 10^9$ | $0.6 \cdot 10^9$ | $1.1 \cdot 10^8$ | $2.7 \cdot 10^8$ | $2 \cdot 10^7$ | $4.7 \cdot 10^7$ |
| II | $2.1 \cdot 10^9$ | $2.3 \cdot 10^9$ | $0.7 \cdot 10^9$ | $0.7 \cdot 10^9$ | $0.8 \cdot 10^8$ | $3.2 \cdot 10^8$ | $0.7 \cdot 10^7$ | $8.5 \cdot 10^7$ |
| III | $0.99 \cdot 10^9$ | $0.9 \cdot 10^9$ | $0.7 \cdot 10^9$ | $0.5 \cdot 10^9$ | $0.9 \cdot 10^8$ | $5.6 \cdot 10^8$ | $3.3 \cdot 10^7$ | $9 \cdot 10^7$ |
| average | $1.5 \cdot 10^9$ | $1.8 \cdot 10^9$ | $0.7 \cdot 10^9$ | $0.6 \cdot 10^9$ | $0.98 \cdot 10^8$ | $3.8 \cdot 10^8$ | $2 \cdot 10^7$ | $7.4 \cdot 10^7$ |
| interval of confidence ($\alpha = 5\%$) | $0.6 \cdot 10^9$ | $0.7 \cdot 10^9$ | $0.1 \cdot 10^9$ | $0.2 \cdot 10^9$ | $0.3 \cdot 10^8$ | $1.6 \cdot 10^8$ | $2 \cdot 10^7$ | $3.5 \cdot 10^7$ |
| | NS | | NS | | $p < 1°/_{oo}$ | | $p = 1\%$ | |

What is claimed is:

1. A device for the transmission of energy comprising a source of energy and a means for transmitting the energy provided by the source, wherein the improvement comprises a means for transmitting energy which comprises a homogeneous mixture of an inorganic crystalline matter in powder form formed of kaolinite and talc, and of a carbohydrate.

2. The device of claim 1, wherein the carbohydrate is glucose.

3. The device of claim 1, wherein the homogeneous mixture has the following composition:
   14.6% by weight of kaolinite,
   72.2% by weight of talc,
   13.2% by weight of carbohydrate.

4. The device of claim 3, wherein the carbohydrate is glucose.

5. The device of claim 1, wherein the means for transmitting the energy further comprises an inert envelope adapted to contain said homogeneous mixture.

6. The device of claim 5, wherein the inert envelope is constituted by cardboard, a sheet of plastics material or wood.

7. The device of claim 1, wherein the source of electrical energy is constituted by a filament embedded in the mixture connected to a source of alternating or direct current.

8. The device of claim 7, wherein the intensity of the current is included between 0.1 mA and 10 A, the voltage between 0.1 and 100 V and, in the case of alternating current, the frequency is between 0.1 Hz and $2.10^9$ Hz.

9. A device for transmission of energy comprising a source of energy and a means for transmitting the energy provided by the source, wherein the means for transmitting the energy comprises a homogeneous mixture of an inorganic crystalline matter in powder form formed by one or more of the group consisting of octahedral and tetrahedral layers of an amorphous, non-crystalline, organic material, the mixture being enclosed in an inert envelope and the enveloped mixture being connected to a source of energy.

10. The device of claim 9 wherein the crystalline matter is selected from the group consisting of kaolinite, serpentine, mica, quartz or asbestos.

11. The device of claim 9 wherein the crystalline matter is talc.

12. The device of claim 9 wherein the organic material is a carbohydrate.

13. The device of claim 9 wherein the organic material is glucose.

14. The device of claim 9 wherein the inert envelope is composed of material selected from the group consisting of card board, sheets of plastic material or wood.

15. The device of claim 9 wherein the homogeneous mixture has the following composition:
   14.6% by weight of kaolinite,
   72.2% by weight of talc,
   13.2% by weight of carbohydrate.

16. The device of claim 9 wherein the source of energy is electrical energy provided by a filament embedded in the mixture and the filament is connected to a source of current.

17. The device of claim 9 wherein the source of energy is an alternating or direct electrical current.

18. The device of claim 17 wherein the intensity of the current is about 0.1 mA to 10 A, the voltage about 0.1 to 100 V and, in the case of alternating current, the frequency is about 0.1 Hz to $2.10^9$ Hz.

19. A process for improving bacterial metabolism comprising placing a device for the transmission of energy, comprising a homogeneous mixture of an inorganic crystalline matter in powder form, formed of kaolinite and talc, and a carbohydrate, and an inert envelop enclosing the mixture and a filament connected to a source of electrical current embedded in the mixture and a bacterial culture medium in an incubator containing additional homogeneous mixture.

* * * * *